(12) United States Patent
Warmbier

(10) Patent No.: US 12,102,703 B2
(45) Date of Patent: Oct. 1, 2024

(54) HAIR DYEING COMPOSITION COMPRISING BLUE DYES

(71) Applicant: KAO CORPORATION, Tokyo (JP)

(72) Inventor: Susann Warmbier, Darmstadt (DE)

(73) Assignee: KAO CORPORATION, Tokyo (JP)

( * ) Notice: Subject to any disclaimer, the term of this patent is extended or adjusted under 35 U.S.C. 154(b) by 56 days.

(21) Appl. No.: 18/043,633

(22) PCT Filed: Sep. 20, 2021

(86) PCT No.: PCT/EP2021/075792
§ 371 (c)(1),
(2) Date: Mar. 1, 2023

(87) PCT Pub. No.: WO2022/069281
PCT Pub. Date: Apr. 7, 2022

(65) Prior Publication Data
US 2023/0270646 A1    Aug. 31, 2023

(30) Foreign Application Priority Data
Sep. 30, 2020    (EP) .................................... 20199264

(51) Int. Cl.
| | | |
|---|---|---|
| *A61Q 5/10* | (2006.01) | |
| *A61K 8/06* | (2006.01) | |
| *A61K 8/22* | (2006.01) | |
| *A61K 8/23* | (2006.01) | |
| *A61K 8/34* | (2006.01) | |
| *A61K 8/36* | (2006.01) | |
| *A61K 8/41* | (2006.01) | |
| *A61K 8/43* | (2006.01) | |
| *A61K 8/44* | (2006.01) | |
| *A61K 8/46* | (2006.01) | |
| *A61K 8/49* | (2006.01) | |

(52) U.S. Cl.
CPC ............... *A61K 8/49* (2013.01); *A61K 8/062* (2013.01); *A61K 8/22* (2013.01); *A61K 8/23* (2013.01); *A61K 8/342* (2013.01); *A61K 8/361* (2013.01); *A61K 8/411* (2013.01); *A61K 8/43* (2013.01); *A61K 8/44* (2013.01); *A61K 8/466* (2013.01); *A61Q 5/10* (2013.01); *A61K 2800/5922* (2013.01); *A61K 2800/882* (2013.01)

(58) Field of Classification Search
CPC . A61K 8/49; A61K 8/062; A61K 8/22; A61K 8/23; A61K 8/342; A61K 8/361; A61K 8/411; A61K 8/43; A61K 8/44; A61K 8/466; A61K 2800/5922; A61K 2800/882; A61K 8/19; A61K 8/41; A61Q 5/10; A61Q 5/08
USPC .......................................................... 8/405
See application file for complete search history.

(56) References Cited

U.S. PATENT DOCUMENTS

| | | | |
|---|---|---|---|
| 2004/0143910 A1 | 7/2004 | Said et al. | |
| 2009/0217466 A1* | 9/2009 | Barbieru | C09B 1/501 |
| | | | 8/405 |
| 2016/0303014 A1* | 10/2016 | Grevalcuore | A45D 7/04 |
| 2017/0258695 A1* | 9/2017 | Consoli | A61K 8/55 |
| 2017/0354581 A1* | 12/2017 | Consoli | A61Q 5/10 |

FOREIGN PATENT DOCUMENTS

| | | |
|---|---|---|
| EP | 1 366 752 A1 | 12/2003 |
| EP | 1 372 581 A1 | 1/2004 |
| JP | 2004-524331 A | 8/2004 |
| JP | 2019-151615 A | 9/2018 |
| WO | WO 02/074270 A1 | 9/2002 |
| WO | WO 2007090800 A2 * 8/2007 ............... A61Q 5/10 |  |

OTHER PUBLICATIONS

International Search Report & Written Opinion issued Mar. 7, 2022 in PCT/EP2021/075792, filed on Sep. 20, 2021, 8 pages.
Extended European Search Report issued Mar. 9, 2021 in European Application 20199264.1, filed on Sep. 30, 2020, 5 pages.

* cited by examiner

*Primary Examiner* — Eisa B Elhilo
(74) *Attorney, Agent, or Firm* — Oblon, McClelland, Maier & Neustadt, L.L.P.

(57) ABSTRACT

A dyeing composition for keratin fibers, including one or more alkalizing agents, HC Blue 18, and tetrabromophenol blue. A method for dyeing keratin fibers, including mixing the dyeing composition with a second aqueous composition having a pH in the range of 1 to 6 and optionally including one or more oxidizing agents to yield a ready-to-use composition having a pH in the range of 7 to 12, applying the ready-to-use composition onto the keratin fibers and leaving it for a time period in the range of 1 min to 60 min, and rinsing-off the keratin fibers and optionally shampooing the keratin fibers.

20 Claims, No Drawings

HAIR DYEING COMPOSITION COMPRISING BLUE DYES

CROSS REFERENCE TO RELATED APPLICATIONS

This application is a National Stage entry under 35 U.S.C. § 371 of PCT/EP2021/075792, filed on Sep. 20, 2021, and claims priority to European Patent Application No. 20199264.1, filed on Sep. 30, 2020. The entire contents of both are incorporated herein by reference.

FIELD OF THE INVENTION

The present invention relates to dyeing compositions, kit-of-parts, and dyeing methods for keratin fibers, preferably human keratin fibers, more preferably human hair.

BACKGROUND OF THE INVENTION

Direct dyes have been of particular interest of cosmetic industry over the past decade. In contrast to their oxidative counterparts, direct dyes are easier to apply to keratin fibers, but often lack vibrancy, color intensity, and color stability over time.

Applicant has developed new direct dyes (EP1366752), which complement the availability and color range of the existing ones. One of the aforementioned developed dyes is HC Blue 18.

Due to its phenolic structure, the color of HC Blue 18 is pH dependent. At low pH (protonated form), it shows a pale beige color and at high pH (deprotonated form), it shows a brilliant blue-violet color. But the consumers expect their hair color to be stable over a broad pH spectrum.

However, most hair care products have a pH range from 4 to 6, which is overlapping with the point at which HC Blue 18 exhibits its color shift. As a result, if the consumer selects a hair care product with a too low pH, the blue dye will lose its color, shift in color tone to beige and the overall hair loses color depth. Needless to say that such shift will be very disappointing to the customer and is highly undesired.

Besides the problem of hair care product selection, the scalp of a subgroup of customers produces sebum with a pH that is lower than that of normal skin. Hence, the dyed root portion of these customers is prone to an undesired color shift, whereas the lengths remain at their originally intended artificial color.

In summary, there is a real need to develop dyeing compositions for keratin fibers, which lead to a stable color over a broad pH range, while being stable over a long storage time. This problem has not been satisfactorily solved by the prior art.

SUMMARY OF THE INVENTION

Therefore, the first object of the present invention is a dyeing composition for keratin fibers, preferably for human keratin fibers, more preferably for human hair, comprising:
   a) one or more alkalizing agent(s),
   b) HC Blue 18 and/or its salt(s),
   c) tetrabromophenol blue and/or its salt(s).

The second object of the present invention is a kit-of-parts comprising
   a first composition comprising compound(s) according to a) and compound(s) according to b) as defined above, and
   a second aqueous composition having a pH in the range of 7 to 12 comprising compound(s) according to a) and compound(s) according to c) as defined above,
   a third aqueous composition having a pH in the range of 1 to 6 and optionally comprising one or more oxidizing agent(s).

The second object of the present invention is a two-part dyeing composition comprising a first composition as defined above and a second aqueous composition having a pH in the range of 1 to 6 and optionally comprising one or more oxidizing agent(s).

The third object of the present invention is a method for dyeing keratin fibers, preferably human keratin fibers, more preferably human hair, comprising the steps of:
   i) mixing the dyeing composition as defined above with a second aqueous composition as defined above for the two-part composition to yield a ready-to-use composition having a pH in the range of 7 to 12,
   ii) applying the ready-to-use composition onto keratin fibers and leaving it for a time period in the range of 1 min to 60 min,
   iii) rinsing-off the keratin fibers and optionally shampooing the keratin fibers.

DETAILED DESCRIPTION OF THE INVENTION

Inventors of the present invention have unexpectedly found out that the combination of HC Blue 18 with another blue dye tetrabromophenol blue leads to highly stable color results over a broad range of pH. The combination of both dyes led to a brilliant, intense, and stable color result on keratin fibers. None of the two dyes used alone was able to simultaneously deliver the brilliancy and pH stability. In addition, the dyeing composition exhibited very good storage stability over time.

Dyeing Composition

The present invention is directed to a dyeing composition for keratin fibers, preferably for human keratin fibers, more preferably for human hair, comprising:
   a) one or more alkalizing agent(s),
   b) HC Blue 18 and/or its salt(s),
   c) tetrabromophenol blue and/or its salt(s).

Compound(s) According to a)

The composition of the present invention comprises one or more alkalizing agent(s) as compound(s) according to a).

It is preferred from the viewpoint of providing alkalinity and cosmetic safety that one or more compound(s) according to a) is/are one or more organic alkalizing agent(s) and/or ammonia and/or its salt(s).

Preferably, one or more organic alkalizing agent(s) are selected from alkyl and/or alkanolamine(s) and/or its/their salt(s), more preferably they/it is selected from monoethanolamine, diethanolamine, monoethanol methylamine, monoethanol dimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, diethanolbutylamine, trimethylamine, triethylamine, 2-amino-2-methylpropanol, tris-(hydroxymethyl)-aminomethan and/or its/their salt(s), and/or their mixtures, from the viewpoint of providing alkalinity and cosmetic safety as well as their low odor.

The most preferred alkalizing agent(s) it is selected from monoethanolamine, 2-amino-2-methylpropanol, tris-(hydroxymethyl)-aminomethan and/or its/their salt(s), ammonia and or its salt(s), and/or their mixtures, from the viewpoint of providing alkalinity and cosmetic safety.

In one aspect of the present invention, it may be suitable from the viewpoint of storage stability that one or more compound(s) according to group a) is one or more inorganic alkalizing agent(s), preferably selected from metasilicates, carbonates, and/or bicarbonates, and/or their alkali or earth alkali salts, and/or their mixtures, preferably it is sodium metasilicate.

It is preferred from the viewpoint of providing alkalinity that the total concentration of compound(s) according to a), preferably the total concentration of one or more alkanolamine(s) and/or its/their salt(s) and/or ammonia and/or its salt(s), is 0.1% by weight or more, more preferably 0.25% by weight or more, further more preferably 0.5% by weight or more, calculated to the total weight of the composition.

It is preferred from the viewpoint of providing alkalinity, hair damage, and odor that the total concentration of compound(s) according to a), preferably the total concentration of one or more alkanolamine(s) and/or its/their salt(s) and/or ammonia and/or its salt(s), is 40% by weight or less, more preferably 30% by weight or less, further more preferably 25% by weight or less, calculated to the total weight of the composition.

For attaining the above-mentioned effects, it is preferred that the total concentration of compound(s) according to a), preferably the total concentration of one or more alkanolamine(s) and/or its/their salt(s) and/or ammonia and/or its salt(s), is in the range of 0.1% to 40% by weight, preferably in the range of 0.25% to 30% by weight, more preferably in the range of 0.5% to 25% by weight, calculated to the total weight of the composition.

Compound(s) According to b)

The dyeing composition of the present invention comprises HC Blue 18 and/or its salt(s) as compound(s) according to b).

It is preferred from the viewpoint of color intensity that the total concentration of compound(s) according to b) is 0.001% by weight or more, further preferably 0.005% by weight or more, still more preferably 0.01% by weight or more, calculated to the total weight of the composition.

It is preferred from the viewpoint of color intensity and economic reasons that the total concentration of compound (s) according to b) is 10% by weight or less, further preferably 5% by weight or less, still more preferably 1% by weight or less, still further more preferably 0.75% by weight or less, calculated to the total weight of the composition.

For attaining the above-mentioned effects, it is preferred that the total concentration of compound(s) according to b) is in the range of 0.001% to 10% by weight, preferably in the range of 0.005% to 5% by weight, more preferably in the range of 0.01% to 1% by weight, still further more preferably in the range of 0.01% to 0.75% by weight, calculated to the total weight of the composition.

Compound(s) According to c)

The dyeing composition of the present invention comprises tetrabromophenol blue and/or its salt(s) as compound (s) according to c).

It is preferred from the viewpoint of color intensity that the total concentration of compound(s) according to c) is 0.001% by weight or more, more preferably 0.01% by weight or more, further preferably 0.02% by weight or more, calculated to the total weight of the composition.

It is preferred from the viewpoint of color intensity and economic reasons that the total concentration of compound (s) according to c) is 10% by weight or less, more preferably 5% by weight or less, further more preferably 1% by weight or less, still further more preferably 0.5% by weight or less, calculated to the total weight of the composition.

For attaining the above-mentioned effects, it is preferred that the total concentration of compound(s) according to c) is in the range of 0.001% to 10% by weight, preferably in the range of 0.01% to 5% by weight, more preferably in the range of 0.02% to 1% by weight, still further more preferably in the range of 0.02% to 0.5% by weight, calculated to the total weight of the composition.

It is further preferred from the viewpoint of color stability over a broad pH range and color intensity that the weight ratio of compound(s) according to c) to compound(s) according to b) is in the range of 0.1 or more, more preferably 0.5 or more, further more preferably 0.8 or more, still further more preferably 5 or more.

It is further preferred from the viewpoint of color stability over a broad pH range and color intensity that the weight ratio of compound(s) according to c) to compound(s) according to b) is in the range of 200 or less, more preferably 160 or less, further more preferably 140 or less, still more preferably 100 or less, further more preferably 50 or less.

For attaining the above-mentioned effects, it is preferred that the weight ratio of compound(s) according to c) to compound(s) according to b) is in the range of 0.1 to 200, preferably on the range of 0.5 to 160, more preferably in the range of 0.8 to 140, still further more preferably in the range of 5 to 100, further more preferably in the range of 5 to 50.

Cosmetic Forms of Composition

The dyeing composition of the present invention is available in various cosmetic forms.

Aqueous Composition

In one aspect of the present invention, the dyeing composition is an aqueous composition.

The term 'aqueous' denotes a composition that comprises a majority of water, i.e., the composition preferably comprises water at 50% by weight or more, further more preferably at 60% by weight or more, still more preferably at 70% by weight or more, still further more preferably at 80% by weight or more, calculated to the total weight of the composition, from the viewpoint of achieving a cosmetically acceptable composition.

It is further preferred from the viewpoint of dyeing intensity that the composition comprises water at 98% by weight or less, more preferably at 95% by weight or less, further more preferably at 92% by weight or less, calculated to the total weight of the composition.

For achieving the above-mentioned effects, it is preferred that the total concentration of water is in the range of 50% to 98% by weight, more preferably in the range of 60% to 95% by weight, further more preferably in the range of 70% to 92% by weight, still more preferably in the range of 80% to 92% by weight, calculated to the total weight of the composition.

It is preferred from the viewpoint of dyeing performance that the pH of the aqueous composition is 7 or more, more preferably the pH is 7.5 or more, further more preferably the pH is 8 or more, still further more preferably the pH is 9 or more.

It is preferred from the viewpoint of hair damage and dyeing performance that the pH of the composition is 12 or less, more preferably the pH is 11 or less, still more preferably the pH is 10.5 or less.

For attaining the above mentioned effects, it is preferred that the aqueous dyeing composition has a pH in the range of 7 to 12, preferably in the range of 7.5 to 11, more preferably in the range of 8 to 10.5, further more preferably in the range of 9 to 10.5.

Thus, the present disclosure is also directed to an aqueous dyeing composition for keratin fibers, preferably for human keratin fibers, more preferably for human hair, having a pH in the range of 7 to 12, preferably in the range of 7.5 to 11, more preferably in the range of 8 to 10.5, further more preferably in the range of 9 to 10.5 comprising:
- a) one or more alkalizing agent(s),
- b) HC Blue 18 and/or its salt(s),
- c) tetrabromophenol blue and/or its salt(s),
- wherein the composition comprises water at 50% by weight or more, calculated to the total weight of the composition.

Liquid Composition Comprising Less than 1% by Weight of Water

In another aspect of the present invention, the dyeing composition is a liquid composition at 25° C. and atmospheric pressure comprising one or more organic solvent(s) as compound(s) according to d) and less than 1% by weight of water, calculated to the total weight of the composition. Preferably, the composition is anhydrous, from the viewpoint of dye stability.

The term 'liquid' denotes a physical state at 25° C. and atmospheric pressure, i.e., the dyeing composition is liquid at room temperature.

The term 'anhydrous' denotes a composition, which is free of added water. This does not exclude the presence of residual moisture from air or crystal water bound to ingredients.

For this aspect of the present invention, the composition may comprise one or more organic solvent(s) as compound(s) according to d).

The organic solvent(s) may be selected to dissolve the compounds a) to c). Preferred solvents are mono-, di-, and trivalent alcohols and/or their mixtures.

Preferred mono-, di-, and trivalent alcohols from the viewpoint of cosmetic safety and dissolution capacity are ethanol, n-propanol, isopropanol, propylene glycol, ethylene glycol, benzyl alcohol, phenoxyethanol, and glycerol, and/or their mixtures.

It is further preferred from the viewpoint of solution stability that the total concentration of compound(s) according to d) is 75% by weight or more, more preferably 80% by weight or more, further more preferably 85% by weight or more, calculated to the total weight of the composition.

It is further preferred from the viewpoint of dyeing intensity that the total concentration of compound(s) according to d) is 98% by weight or less, more preferably 95% by weight or less, further more preferably 92% by weight or less, calculated to the total weight of the composition.

For attaining the above-mentioned effects, it is preferred that the total concentration of compound(s) according to d) is in the range of 75% to 98% by weight, more preferably 80% to 95% by weight, further more preferably in the range of 85% to 92% by weight, calculated to the total weight of the composition.

Thus, the present disclosure is also directed to an anhydrous dyeing composition for keratin fibers, preferably for human keratin fibers, more preferably for human hair, comprising:
- a) one or more alkalizing agent(s),
- b) HC Blue 18 and/or its salt(s),
- c) tetrabromophenol blue and/or its salt(s),
- d) one or more organic solvent(s), wherein the total concentration of compound(s) according to d) is 75% by weight or more, calculated to the total weight of the composition.

Powder Composition

In one aspect of the present invention, the dyeing composition may be a powder composition.

The term 'powder' denotes a solid composition at 25° C. and atmospheric pressure. The term relates to freely flowing powders as well as compressed powders such as tablets. The powder composition may also comprise water as long as its nature of the solid state at 25° C. is unchanged. Depending on the type of powder, a water content of 10% by weight or more, calculated to the total weight of the composition, may be acceptable. This does not exclude the presence of residual moisture from air or crystal water bound to ingredients.

It is preferred from the viewpoint of composition stability and convenience of use that the dyeing composition comprises one or more pulverulent excipient as compound(s) according to e).

The term 'excipient' denotes a compound, which may act as filling material and dispersant for the other compounds of the dyeing composition and do not react with the dyes and the alkalizing agent, and, thus, confer the powder a high degree of storage stability over an extended period of time.

The dyeing composition of the present invention may comprise an organic and/or an inorganic pulverulent excipient in which the alkalizing agent and direct dyes are dispersed.

Suitable organic and/or an inorganic pulverulent excipients are, for example, diatomaceous earth, kaolin, bentonite, starch especially corn, tapioca, rice, wheat and potato, nylon powder, montmorillonit, gypsum, sawdust and perlite.

The total concentration of organic and/or an inorganic pulverulent excipient preferably is 50% by weight or more, more preferably 55% by weight or more, further more preferably 60% by weight or more, still further more preferably 65% by weight or more, even further more preferably 70% by weight or more, even more preferably 75% by weight or more, calculated to the total of the composition, from the viewpoint of achieving good dispersability of the direct dyes in the powder and quick dissolution of the powder.

The total concentration of organic and/or an inorganic pulverulent excipient preferably is 98% by weight or less, more preferably 95% by weight or less, further more preferably 90% by weight or less, calculated to the total of the composition, from the viewpoint of achieving good dispersability of the direct dyes in the powder and formulation freedom.

For attaining the above mentioned effects, the total concentration of organic and/or an inorganic pulverulent excipient preferably is in the range of 50% to 98% by weight, more preferably in the range of 55% to 95% by weight, further more preferably in the range of 60% to 90% by weight, still further more preferably 65% to 90% by weight, still further more preferably 70% to 90% by weight, even more preferably 75% to 90% by weight, calculated to the total of the composition.

Thus, the present disclosure is also directed to a dyeing composition for keratin fibers, preferably for human keratin fibers, more preferably for human hair, comprising:
- a) one or more alkalizing agent(s),
- b) HC Blue 18 and/or its salt(s),
- c) tetrabromophenol blue and/or its salt(s),
- e) one or more pulverulent excipient(s),
- wherein the composition is a powder composition, and preferably wherein the total concentration of compound(s) according to e) is 50% by weight or more, calculated to the total weight of the composition.

Lipophilic Compound(s) According to f)

It is preferred that the dyeing composition of the present invention comprises one or more lipophilic compound(s) as compound(s) according to f).

The term 'lipophilic' denotes a liquid compound at 25° C. and atmospheric pressure and does not fully mix with water under the aforementioned conditions.

Preferably, lipophilic compounds are selected from fatty alcohols, fatty acids, waxes, vegetable oils, petrolatum based products, silicones, aminated silicones, and compounds according to the general structure:

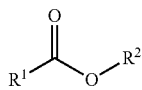

wherein R1 is selected from linear or branched, saturated or unsaturated alkyl with C11 to C21 and optionally modified with 1 hydroxyl group, and R2 is selected from linear or branched, saturated or unsaturated alkyl with C3 to C18, preferably the compound is ethylhexyl hydroxystearate, in the viewpoint of film homogeneity and pigment deposition Suitable fatty alcohols are linear or branched, saturated or unsaturated fatty alcohols with C12 to C22 are lauryl alcohol, tridecyl alcohol, myristyl alcohol, pentadecyl alcohol, cetyl alcohol, palmitoleyl alcohol, heptadecyl alcohol, stearyl alcohol, nonadecyl alcohol, arachidyl alcohol, behenyl alcohol, and/or their mixtures.

Suitable fatty acids are saturated or unsaturated fatty acids with or without a hydroxyl group. Suitable are myristoleic acid, palmitoleic acid, oleic acidlinoleic acid, arachidonic acid, and/or their mixtures.

Suitable compounds according to the general structure from above:

are isopropyl palmitate, isopropyl myristate, octyl palmitate, isocetyl palmitate, octyl stearate, oleyl oleate, ethylhexyl hydroxystearate, myristyl myristate, behenyl behenate, and/or their mixtures.

Suitable vegetable oils are jojoba oil, avocado oil, sunflower seed oil, walnut oil, peanut oil, olive oil, rapeseed oil, cottonseed oil, palm oil, sesame oil, soybean oil, coconut oil, safflower oil, almond oil, macadamia nut oil, grapefruit seed oil, lemon kernel oil, orange kernel oil, apricot kernel oil, castor oil, and/or their mixtures.

Suitable petrolatum-based products are liquid paraffins, especially paraffinum perliquidum and paraffinum subliquidum, and mineral oil, in particular white mineral oil, and/or their mixtures.

Suitable silicones are dimethylpolysiloxanes, and modified silicones (for example, amino-modified silicones, fluorine-modified silicones, alcohol-modified silicones, polyether-modified silicones, epoxy-modified silicones, or alkyl-modified silicones), but dimethylpolysiloxane, polyether-modified silicones and amino-modified silicones are preferred. Amino-modified silicones are commonly known under their CTFA name amodimethicone.

Specific examples of suitable commercially available amodimethicone oils such as SF8452C, SS-3551 (all by Dow Corning Toray Co., Ltd.), KF-8004, KF-8675, and KF-8015 (all by Shin-Etsu Chemical Co., Ltd.), and amodimethicone emulsions such as SM8704C, SM8904, BY22-079, FZ-4671, and FZ-4672 (all by Dow corning Toray Co., Ltd.).

The amino-modified silicone may be any silicone having an amino group or a quaternary ammonium group, and examples thereof include amine-modified silicone oil having all or a part of the terminal hydroxyl groups capped with a methyl group for example, and an amodimethicone which does not have the terminals capped.

The composition may comprise one or more waxes. Suitable non-limiting and preferred examples are petrolatum, ozokerit, carnauba wax, paraffin, lanolin wax, candelila wax, bees wax, microcrystalline wax and cocoglycerides.

The dyeing composition may comprise lipophilic compound(s) according to f) form the viewpoint of dyeing intensity, preferably at a total concentration of 0.1% by weight or more, more preferably at 0.5% by weight or more, further more preferably at 1% by weight or more, calculated to the total weight of the composition.

The dyeing composition may comprise lipophilic compound(s) according to f) form the viewpoint of dyeing intensity and rinsibility of keratin fibers, preferably at a total concentration of 40% by weight or less, more preferably at 30% by weight or less, further more preferably at 25% by weight or less, calculated to the total weight of the composition.

For attaining the above mentioned effects, it is preferred that the dyeing composition comprises lipophilic compound(s) according to f) at a total concentration in the range of 0.1% to 40% by weight, more preferably in the range of 0.5% to 30% by weight, further more preferably in the range of 1% to 25% by weight, calculated to the total weight of the composition.

In one aspect of the present invention, the disclosure is also directed to an aqueous dyeing composition for keratin fibers, preferably for human keratin fibers, more preferably for human hair, having a pH in the range of 7 to 12, preferably in the range of 7.5 to 11, more preferably in the range of 8 to 10.5, further more preferably in the range of 9 to 10.5 comprising:
  a) one or more alkalizing agent(s),
  b) HC Blue 18 and/or its salt(s),
  c) tetrabromophenol blue and/or its salt(s),
  wherein the composition comprises water at 50% by weight or more, calculated to the total weight of the composition, and
  wherein the composition is an emulsion and comprises one or more compound(s) according to f) selected from fatty alcohols having an branched or linear, saturated or unsaturated carbon chain length in the range of C12 to C22, fatty acids having an branched or linear, saturated or unsaturated carbon chain length in the range of C12 to C22, ester oils, vegetable oils, silicone oil, paraffin oils.

In another aspect of the present invention, the disclosure also relates to a dyeing composition for keratin fibers, preferably for human keratin fibers, more preferably for human hair, comprising:
  a) one or more alkalizing agent(s),
  b) HC Blue 18 and/or its salt(s),
  c) tetrabromophenol blue and/or its salt(s),
  e) one or more pulverulent excipient(s),
  wherein the composition is a powder composition, and preferably wherein the total concentration of compound(s) according to e) is 50% by weight or more, calculated to the total weight of the composition, and wherein the composition comprises one or more lipophilic compound(s) according to f), preferably at a total concentration of 1% by weight or more.

The artisan will note that the latter composition is either a dust-free dyeing powder or a dyeing paste.

Surfactants as Compound(s) According to g)

It is further preferred from the viewpoint of mixability of the dyeing composition and wetting of keratin fibers that the composition of the present invention further comprises one or more surfactant(s) as compound(s) according to g), more preferably selected from non-ionic, cationic, anionic, zwitterionic/amphoteric surfactant(s).

Anionic surfactants suitable are in principle known from the cleansing compositions. These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates. Preferred anionic surfactants are alkyl sulphate surfactants especially lauryl sulphate and its salts.

Further suitable surfactants are nonionic surfactants. Non-limiting examples are long-chain fatty acid mono- and dialkanolamides, such as coco fatty acid mono- or diethanolamide and myristic fatty acid mono or diethanolamide, stearic acid mono or diethanolamide, alkyl polyglucosides with an alkyl group of 8 to 18 carbon atoms, and with 1 to 5 glucoside units, sorbitan esters, such as polyethylene glycol sorbitan stearic, palmitic, myristic and lauric acid esters, fatty acid polyglycol esters or poly-condensates of ethyleneoxide and propyleneoxide, as they are on the market, for example, under the trade name "PluronicsR", as well as fatty alcohol ethoxylates, $C_{10}$-$C_{22}$-fatty alcohol ethoxylates, known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 100, preferably about 10 and about 30.

Suitable amphoteric/zwitterionic surfactants are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate are also suitable.

Typical cationic surfactants are cetyl trimethyl ammonium chloride, stearyl trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

It is preferred from the viewpoint of composition stability, wetting of keratin fibers, and ingredient dispersability that the total concentration of compound(s) according to g) is 0.1% by weight or more, preferably 0.2% by weight or more, further more preferably 0.25% by weight or more, calculated to the total weight of the composition.

It is preferred from the viewpoint of composition stability, wetting of keratin fibers, and ingredient dispersability that the total concentration of compound(s) according to g) is 5% by weight or less, preferably 4% by weight or less, further more preferably 2.5% by weight or less, calculated to the total weight of the composition.

For attaining the above-mentioned effects, it is preferred that the total concentration of compound(s) according to g) is in the range of 0.1% to 5% by weight, more preferably 0.2% to 4% by weight, further more preferably 0.2% to 2.5% by weight, calculated to the total weight of the composition.

Dyes Different from b) and c)

The dyeing composition of the present invention may comprise one or more dye compound(s) different from groups b) and c), preferably selected from oxidative dye precursor(s), oxidative dye coupler(s), and/or direct dye(s).

Suitable oxidative dye precursors classes are p-phenylendiamines, p-aminophenols, and heterocyclic compounds such as diaminopyrazols and substituted pyrimidines, and suitable coupling substances are resorcinols, m-aminophenols, m-phenylendiamines, pyridines and substituted derivatives, and naphthols.

Suitable oxidative dye couplers are 5-amino-2-methylphenol, 2-methyl-5-hydroxyethylaminophenol, 2,4-diaminophenoxyethanol, 2-amino-4-hydroxyethylaminoanisol, 2-methyl-5-amino-6-chlorphenol, 1,3-bis(2,4-diaminophenoxy)propane, 2-bis(2-hydroxyethyl)aminotoluene, 2-amino-5-methylphenol, resorcinol, 2-methyl-resorcinol, 4-chlororesorcinol, 2-amino-4-chlorophenol, 5-amino-4-methoxy-2-methylphenol, 2-am inophenol, 3-amino-phenol, 1-methyl-2-hydroxy-4-aminobenzene, 3-N,N-dimethyl am inophenol, 2,6-dihydroxy-3,5-dimethoxypyridine, 5-amino-3-methylphenol, 6-amino-3-methylphenol, 1,3-diamino-benzene, 1-amino-3-(2'-hydroxyethylamino)benzene, 1-amino-3-[bis(2'-hydroxy-ethyl) amino] benzene, α-naphthol, 4,6-dichlororesorcinol, 1,3-diaminotoluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)-benzene, and/or their salts, and/or their mixtures.

The dyeing composition of the present invention may comprise the oxidative dye couplers and/or precursors at approximately the equimolar proportions, for example at a total concentration in the range of 0.001 to 5%, calculated to the total weight of the composition.

Direct dyes other than compounds according to groups b) and c) may be selected from cationic, anionic and/or non-ionic direct dyes.

The total concentration of one or more direct dyes other than compounds according to groups b) and c) in the composition of the present invention, if present, preferably is 0.01% by weight or more, more preferably 0.05% by weight or more, further more preferably 0.1% by weight or more, calculated to the total weight of the composition, from the viewpoint of sufficiently dyeing the keratin fibers.

The total concentration of one or more direct dyes other than compounds according to groups b) and c) in the composition of the present invention, if present, preferably is 10% by weight or less, more preferably 9% by weight or less, further more preferably 7.5% by weight or less, further more preferably 6% by weight or less, even more preferably 4% by weight or less, calculated to the total weight of the composition, from the viewpoint of economic reasons and formulation freedom.

For attaining the above mentioned effects, the total concentration of one or more direct dyes other than compounds according to groups b) and c) in the composition of the present invention, if present, is in the range of 0.01% to 10% by weight, preferably 0.05% to 9% by weight, more preferably 0.1% to 7.5% by weight, further more preferably 0.1% to 6% by weight, even more preferably 0.1% to 4% by weight, calculated to the total weight of the composition.

Thickening Polymers

It is advantageous from the viewpoint of cosmetic safety that the composition of the present invention further comprises one or more thickening polymer(s).

Preferably, the thickening polymers are selected from polymers resulting in an aqueous solution and/or aqueous dispersion at pH between 8 and 10 having a viscosity of at least 5,000 mPa·s measured at a polymer concentration of 1% by weight in water at 25° C., calculated to the total weight of the composition, determined by a Brookfield viscometer, such as at 10 rpm for 1 min, with an appropriate spindle at 25° C.

Suitable non-ionic thickening polymers are cellulose-based polymers. Suitable examples of cellulose-based polymers are methylcellulose, hydroxymethylcellulose, hydroxyethylcellulose, hydroxypropylcellulose, hydroxyethyl-methylcellulose, and alkylated hydroxyl celluloses such as (C2-C8)-alkylcelluloses or cetyl hydroxyethylcellulose.

Suitable anionic thickening polymers are selected from naturally-based anionic polymers and/or synthetic anionic polymers.

Suitably, the natural anionic polymer(s) may be selected from xanthan gum, dehydroxanthan gum, hydroxypropylxanthan gum, carboxymethyl cellulose and starch based polymers such as vegetable starch and/or their synthetically modified derivatives such as hydroxypropyl starch phosphate. Equally suitable are alginic acids, sodium alginates, ammonium alginates, calcium alginates, gum arabic, and guar gum.

The preferred thickening polymer for the composition of the present invention are natural anionic polymers, more preferably xanthan gum and/or dehydroxanthan gum, from the viewpoint of their biodegradability and low environmental impact.

Preferably, the total concentration of thickening polymers of the present invention are 0.1% by weight or more, more preferably 0.25% by weight or more, more preferably 0.5% by weight or more, calculated to the total weight of the composition, from the viewpoint of providing sufficient viscosity to the composition.

Preferably, the total concentration of thickening polymers of the present invention are 15% by weight or less, more preferably 12% by weight or more, further more preferably 10% by weight or less, calculated to the total weight of the composition, from the viewpoint of providing sufficient viscosity to the composition and cost of goods.

For attaining the above-mentioned effects, it is preferred that the total concentration of thickening polymers in the composition of the present invention is in the range of 0.1% to 15% by weight, preferably 0.25% to 12% by weight, more preferably in the range of 0.5% to 10% by weight, calculated to the total weight of the composition.

Two-Part Composition

The present invention is also directed to a two-part dyeing composition comprising
a first composition as defined above, and
a second aqueous composition having a pH in the range of 1 to 6 and optionally comprising one or more oxidizing agent(s).

The second aqueous composition preferably comprises hydrogen peroxide as an oxidizing agent. Suitable concentration range from 0.1% to 20% by weight, preferably 0.25% to 15% by weight, and more preferably 0.5% to 12% by weight, calculated to the total weight of the second aqueous composition.

The pH of the second aqueous composition preferably is in the range of 1.5 to 5, more preferably in the range of 2 to 4.5, adjusted by suitable acids and bases.

It is further preferred from the viewpoint of mixability with the first composition that the second aqueous composition comprises one or more lipophilic compound(s) according to f), as laid out above for the dyeing composition. In such a case, the second aqueous composition is an emulsion and preferably also comprises one or more surfactant(s) as compound(s) according to g), as laid out above for the dyeing composition.

First and second compositions in this aspect of the present invention are intended to be mixed directly prior to application onto keratin fibers.

Kit-of-Parts

The present invention is also directed to a kit-of-parts comprising:
a first composition comprising compound(s) according to a) and compound(s) according to b) as defined above, and
a second aqueous composition having a pH in the range of 7 to 12 comprising compound(s) according to a) and one or more compound(s) according to c) as defined above, and
a third aqueous composition having a pH in the range of 1 to 6 and optionally comprising one or more oxidizing agent(s).

It is preferred that for this aspect of the present invention, the first composition is an anhydrous liquid composition as defined above, but without compound(s) according to c). Except for the latter fact, the disclosure from above also relates to the first anhydrous compositions.

It is preferred that for this aspect of the present invention, the second aqueous composition is an aqueous dyeing composition as defined above, but without compound(s) according to b). Optionally, compound(s) according to a) may be present. Except for the compound(s) according to b), the disclosure from above also relates to the second aqueous composition compositions.

It is preferred that for this aspect of the present invention, the third aqueous composition is an aqueous oxidizing composition, as defined above as second composition for the two-part composition.

The three compositions of the kit are intended to be mixed directly prior to their use onto keratin fibers.

Method for Dyeing

The present invention is also directed to a method for dyeing keratin fibers, preferably human keratin fibers, more preferably human hair, comprising the steps of:
i) mixing the dyeing composition as defined above with a second aqueous composition as defined for the two-part composition to yield a ready-to-use composition having a pH in the range of 7 to 12,
ii) applying the ready-to-use composition onto keratin fibers and leaving it for a time period in the range of 1 min to 60 min,
iii) rinsing-off the keratin fibers and optionally shampooing the keratin fibers.

It is preferred from the viewpoint of color intensity that the pH of the ready-to-use composition as defined in step i) is in the range of 8 to 11, more preferably in the range of 8.5 to 10.5.

It is further preferred from the viewpoint of dyeing intensity and dyeing method economy that the leave-on time as defined in step ii) is in the range of 2 min to 45 min, more preferably in the range of 5 min to 40 min, further more preferably in the range of 10 min to 30 min.

The following examples are to illustrate the invention, but not to limit it.

EXAMPLES

Example 1

The following dyeing compositions of table 1 were prepared by dissolving the alkalizing agent first, and then subsequently adding the dyes to water. Finally, the pH was adjusted.

TABLE 1

| | | Ingredients | Comparative 1 | Inventive 1 | Inventive 2 | Inventive 3 | Inventive 4 | Inventive 5 | Comparative 2 |
|---|---|---|---|---|---|---|---|---|---|
| Composition [% by weight] | a) | Ammonia (28% w/w) | 10 | 10 | 10 | 10 | 10 | 10 | 10 |
| | b) | HC Blue 18 | 0.033 | 0.0297 | 0.0231 | 0.0165 | 0.0099 | 0.0033 | — |
| | c) | Tetrabromophenol blue | — | 0.05 | 0.15 | 0.25 | 0.35 | 0.45 | 0.5 |
| | — | Weight ratio c) to b) | — | 1.68 | 6.5 | 15.1 | 35.4 | 136.4 | — |
| | | NaOH/HCl | | | | Ad pH 10.4 | | | |
| | | Water | | | | Ad 100.0 | | | |
| Evaluation | | $\Delta E^*_1$ [pH 5.5] | 20.6 | 16.58 | 15.83 | 13.38 | 12.86 | 12.16 | 7.95 |
| | | $\Delta E^*_2$ [pH 4.5] | 31.99 | 23.15 | 21.46 | 20.05 | 19.75 | 19.90 | 11.70 |
| | | $\Delta E^*_2 - \Delta E^*_1$ | 11.39 | 6.57 | 5.63 | 6.67 | 6.37 | 7.74 | 3.75 |
| | | Visual appearance | Red-blue | Slightly Red, blue | Neutral blue | Neutral blue | Neutral blue | Blue, slightly green | Blue-green |

The compositions from above were then mixed in a weight ratio of 1:1 with an aqueous oxidizing composition comprising hydrogen peroxide at 6% by weight and phosphoric acid to adjust the pH to 3.5. The resulting ready-to-use compositions had a pH around 10.1.

The ready-to-use compositions were then applied onto yak keratin fibers and left for 30 min at 40° C. Then the fibers were rinsed-off with lukewarm water, shampooed, and blow-dried.

The dyed hair streaks were then treated immersed into a buffered solution having either pH 5.5 or pH 4.5 for 1 min, and then allowed to rest for 5 more min. Then the hairstreaks were blotted dry and allowed to air-dry. The $\Delta E^*_1$ was measured on the hair streaks treated with the buffer solution at pH 5.5, whereas the $\Delta E^*_2$ values were determined on the hair streaks treated with the pH 4.5 buffer solution. The colormetric measurements were obtained with a color-difference meter by the CIE colorimetric system (L*,a*,b*), and the color difference ($\Delta E^*$) were calculated by the following formula.

$$\Delta E^* = (L^*_1 - L^*_0)^2 + (a^*_1 - a^*_0)^2 + (b^*_1 - b^*_0)^2$$

Visual appearance was judged with the naked human eye on the pH 4.5 treated streaks.

As a result, comparative composition 1 had the strongest color intensity at both pH values (highest $\Delta E^*$ values within the row), but also the strongest color shift between pH 5.5 and pH 4.5. Comparative composition 2 had the lowest color shift, but also the lowest color intensity among all tested compositions. The combination of dyes b) and c) resulted in overall better dyeing intensity and much lower sensitivity to pH shifts from 5.5 to 4.5.

Example 2

The following compositions were prepared the same way as explained in example 1: The same mixtures, tests and measurements were conducted.

TABLE 2

| | Ingredients | Comparative 6 | Inventive 6 | Comparative 7 | Inventive 7 | Comparative 8 | Inventive 8 |
|---|---|---|---|---|---|---|---|
| Composition [% by weight] | a) Monoethanolamine | 3.5 | 3.5 | 3.5 | 3.5 | 3.5 | 3.5 |
| | b) HC Blue 18 | 0.02 | 0.02 | 0.13 | 0.13 | 0.34 | 0.34 |
| | c) Tetrabromophenol blue | — | 0.027 | — | 0.27 | — | 0.27 |
| | — Weight ratio c) to b) | — | 1.34 | — | 2.10 | — | 0.80 |
| | NaOH/HCl | | | Ad pH 10.4 | | | |
| | Water | | | Ad 100.0 | | | |
| Evaluation | $\Delta E^*_1$ [pH 5.5] | 11.29 | 9.89 | 15.24 | 11.15 | 16.61 | 12.80 |
| | $\Delta E^*_2$ [pH 4.5] | 18.51 | 14.81 | 21.66 | 15.73 | 22.76 | 16.86 |
| | $\Delta E^*_2 - \Delta E^*_1$ | 7.21 | 4.92 | 6.41 | 4.58 | 6.51 | 4.07 |
| | Visual appearance | Red-blue | Neutral blue | Red-blue | Neutral blue | Red-blue | Neutral blue |

As a results, independently of the concentration of HC Blue 18, the addition of the blue dye according to c) shifted the color from red-blue to neutral blue. Moreover, the differences between pH 5.5 and pH 4.5 treatment became less pronounced.

Example 3

The following oxidative dyeing composition was prepared. An aqueous phase consisting of surfactant and water was heated to 80° C. Simultaneously, a lipophilic phase consisting of fatty alcohol and oleic acid was heated to 80° C. Both of the phases were unified under mixing and stirred until room temperature was reached. Then the hair dyes and residual ingredients were added to the composition by dissolving them in the resulting emulsion.

| | Ingredients | Comp. 9 | Inv. 9 |
|---|---|---|---|
| e) | Cetearyl alcohol | 12.0 | 12.0 |
| f) | Sodium cetearyl sulfate | 2.0 | 2.0 |
| | Cocamide MEA | 5.0 | 5.0 |
| | Oleic acid | 2.0 | 2.0 |
| | Tetrasodium EDTA | 1.0 | 1.0 |
| | Sodium sulfite | 1.0 | 1.0 |
| a) | Ammonium hydroxide | 5.0 | 5.0 |
| a) | Ammonium chloride | 1.0 | 1.0 |
| | Toluene-2,5-Diamine sulfate | 0.75 | 0.75 |
| | Resorcinol | 0.10 | 0.10 |
| | 4-Chlorresorcinol | 0.25 | 0.25 |
| | m-Aminophenol | 0.05 | 0.05 |
| | 4-Amino-2-Hydroxytoluene | 0.05 | 0.05 |
| b) | HC Blue 18 | 0.15 | 0.15 |
| c) | Tetrabromophenol blue | — | 0.5 |
| | Fragrance | 0.5 | 0.5 |
| | NaOH/HCl | pH ad 9.9 | |
| | Water | Ad 100.0 | |

The following oxidative composition was prepared:

| | % by weight |
|---|---|
| Cetearyl alcohol | 2.0 |
| Salicylic Acid | 0.1 |
| Etidronic Acid | 0.2 |
| Phosphoric acid | 0.3 |
| Sodium Lauryl Sulfate | 1.0 |
| Hydrogen Peroxide | 6.0 |
| Water | to 100 |

The oxidative dyeing compositions of above were mixed in the weight ratio of 1:1 directly prior to application onto hair with the oxidizing composition of above. 1 g of each ready-to-use composition was then applied to 2 g of yak hair fibers. The same tests and measurements were conducted as explained for examples 1 and 2.

TABLE 3

| Ingredients | Comp. 9 | Inv. 9 |
|---|---|---|
| $\Delta E^*_1$ [pH 5.5] | 3.59 | 2.38 |
| $\Delta E^*_2$ [pH 4.5] | 9.58 | 3.29 |
| $\Delta E^*_2 - \Delta E^*_1$ | 5.99 | 0.91 |
| Visual appearance | Yellow-brown | Dark brown |

The following examples are within the scope of the present invention.

Example 4

Stability testing of the following composition were conducted at room temperature for 6 weeks. The color of the tested compositions was then observed by the naked human eye.

| | Ingredients | Comp. 10 | Inventive 1 |
|---|---|---|---|
| Composition [% by weight] | a) Ammonia (28%) | 10 | 10 |
| | b) HC Blue 18 | 0.0297 | 0.0297 |
| | — HC Blue 15 | 0.05 | — |
| | c) Tetrabromophenol blue | — | 0.05 |
| | — Weight ratio c) to b) | — | 1.68 |
| | NaOH/HCl | Ad pH 10.4 | |
| | Water | Ad 100.0 | |
| Evaluation | Visual appearance | Intensitve red | Intensive Blue |

Thus, HC Blue 15 was not found stable and shifted its color to red, whereas the inventive composition exhibited good storage stability.

Example 5

The following dyeing composition can be produced by conventional formulation techniques.

|  | % by weight |
| --- | --- |
| Aminomethyl propanol | 5.0 |
| HC Blue 18 | 0.7 |
| Tetrabromophenol blue | 0.5 |
| 1,2-propylene glycol | ad 100.0 |

Example 6

The following dyeing composition can be produced by conventional formulation techniques.

|  | % by weight |
| --- | --- |
| Aminomethyl propanol | 5.0 |
| HC Blue 18 | 0.7 |
| Tetrabromophenol blue | 0.5 |
| Diatomaceous Earth | to 100 |

The invention claimed is:

1. A dyeing composition for keratin fibers, comprising:
one or more alkalizing agents;
HC Blue 18 and/or a salt thereof; and
tetrabromophenol blue and/or a salt thereof.

2. The composition according to claim 1, wherein the one or more alkalizing agents is selected from the group consisting of an organic alkalizing agent, ammonia, and salts thereof.

3. The composition according to claim 1, wherein a total concentration of the one or more alkalizing agents is in the range of 0.1% to 40% by weight, calculated to the total weight of the composition.

4. The composition according to claim 1, wherein a total concentration of the HC Blue 18 is in the range of 0.001% to 10% by weight, calculated to the total weight of the composition.

5. The composition according to claim 1, wherein a total concentration of the tetrabromophenol blue is in the range of 0.001% to 10% by weight, calculated to the total weight of the composition.

6. The composition according to claim 1, wherein a weight ratio of the tetrabromophenol blue to the HC Blue 18 is in the range of 0.1 to 200.

7. The composition according to claim 1, wherein the composition is an aqueous composition, and has a pH in the range of 7 to 12.

8. The composition according to claim 1, wherein the composition is a liquid composition at 25° C. and atmospheric pressure,
wherein the composition further comprises one or more organic solvents, and
wherein the composition has less than 1% by weight of water, calculated to the total weight of the composition.

9. The composition according to claim 1, wherein the composition is a powder composition, and optionally comprises one or more pulverulent excipients.

10. The composition according to claim 1, further comprising one or more lipophilic compounds.

11. The composition according to claim 1, wherein the composition is an emulsion and wherein the composition further comprises a lipophilic compound selected from the group consisting of fatty alcohols having a branched or linear, saturated or unsaturated carbon chain length in the range of C12 to C22, fatty acids having a branched or linear, saturated or unsaturated carbon chain length in the range of C12 to C22, ester oils, vegetable oils, silicone oil, and paraffin oils.

12. The composition according to claim 1, further comprising one or more surfactants.

13. The composition according to claim 1, further comprising one or more dye compounds different from tetrabromophenol blue and HC Blue 18.

14. A dyeing composition, comprising:
the composition of claim 1; and
an aqueous composition having a pH in the range of 1 to 6 and optionally comprising one or more oxidizing agents.

15. A kit comprising:
a first composition comprising one or more alkalizing agents, and HC Blue 18;
a second aqueous composition having a pH in the range of 7 to 12 comprising one or more alkalizing agents, and tetrabromophenol blue; and
a third aqueous composition having a pH in the range of 1 to 6 and optionally comprising one or more oxidizing agents.

16. A method for dyeing keratin fibers, comprising:
mixing the composition of claim 1 with a second aqueous composition having a pH in the range of 1 to 6 and optionally comprising one or more oxidizing agents to yield a ready-to-use composition having a pH in the range of 7 to 12;
applying the ready-to-use composition onto the keratin fibers and leaving it for a time period in the range of 1 min to 60 min; and
rinsing-off the keratin fibers and optionally shampooing the keratin fibers.

17. The composition according to claim 1, wherein the one or more alkalizing agents is selected from the group consisting of monoethanolamine, diethanolamine, monoethanol methylamine, monoethanol dimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, diethanolbutylamine, trimethylamine, triethylamine, 2-amino-2-methylpropanol, tris-(hydroxymethyl)-aminomethane, and salts thereof.

18. The composition according to claim 1, wherein a weight ratio of the tetrabromophenol blue to the HC Blue 18 is in the range of 5 to 50.

19. The composition according to claim 1, wherein the composition is an aqueous composition, and has a pH in the range of in the range of 8 to 10.5.

20. The composition according to claim 1, further comprising one or more surfactants selected from the group consisting of non-ionic, cationic, anionic, and zwitterionic/amphoteric surfactants.

* * * * *